United States Patent [19]
Sever, Jr.

[11] Patent Number: 5,736,986
[45] Date of Patent: Apr. 7, 1998

[54] VIRTUAL REALITY MENTAL CONDITIONING MEDIUM

[76] Inventor: Frank Sever, Jr., 2220 N. Columbus St., Arlington, Va. 22207

[21] Appl. No.: 639,933

[22] Filed: Apr. 26, 1996

Related U.S. Application Data

[63] Continuation-in-part of Ser. No. 502,362, Jul. 14, 1995.
[51] Int. Cl.$^6$ ................................................. A63B 24/00
[52] U.S. Cl. .................................... 345/419; 434/247
[58] Field of Search .................................. 395/119, 118, 395/120; 128/774; 434/307, 247; 463/36; 345/418, 419, 420

[56] References Cited

U.S. PATENT DOCUMENTS

| | | | |
|---|---|---|---|
| 4,060,915 | 12/1977 | Conway | 434/307 R |
| 5,229,756 | 7/1993 | Kosugi et al. | 463/36 |
| 5,429,140 | 7/1995 | Burdea et al. | 128/774 |

*Primary Examiner*—Phu K. Nguyen
*Assistant Examiner*—Cliff N. Vo
*Attorney, Agent, or Firm*—Frank Sever, Jr. Esq. & Associates, P.L.C.

[57] ABSTRACT

The instant invention provides an article of manufacture comprising providing a computer program operable within a virtual reality device which is designed for perfecting mental visualization within the mind of a subject sufficient alone to effect a desired neurological and/or physiological change within the body of said subject, even in the substantial absence of any physical movement by said subject. It also provides the program in combination with a virtual reality device and a method of using the same. The steps of the method include: operatively interfacing the program with the device and mounting the device on the subject; and, running the program. The program can be designed to communicate a metaphoric or real, or combined real and metaphoric scenario to the subject which is designed for perfecting mental visualization within the mind of the subject sufficient alone to effect a desired neurological and/or physiological change within the body of said subject, even in the substantial absence of any physical movement by said subject. It can also be further designed to effect preconditioning of the subject's mind, such as inducing a state of meditation or hypnosis, or combinations thereof. The scenario of the program can be designed to exist in real time, real space, compressed time, compressed space, expanded time, expanded space, or any combination thereof; real or metaphoric or any combination of real and metaphoric. Optionally the program is further designed to enable (motor) interaction between the subject and/or an operator external to the preconditioning and the device.

17 Claims, No Drawings

VIRTUAL REALITY MENTAL CONDITIONING MEDIUM

RELATED APPLICATIONS

This is a Continuation-in-part of application Ser. No. 08/502,362, filed Jul. 4, 1995, entitled: VIRTUAL REALITY METAPHORIC MENTAL CONDITIONING MEDIUM.

BACKGROUND OF THE INVENTION

This invention in its broadest aspects contemplates the application of virtual reality technology for perfecting the mental visualization skills of a subject sufficient alone to effect a desired neurological and/or physiological change within the body of said subject, even in the substantial absence of any physical movement by said subject.

DESCRIPTION OF THE PRIOR ART

The emerging art of virtual reality is now becoming well known as exemplified by the following prior art references which are incorporated herein by reference in their entireties:

U.S. Pat. No. 5,394,517; issued Feb. 28, 1995; assigned to BRITISH AEROSPACE; and classified at United State Patent Office (USPTO) classification(s)/ subclassification(s) 395/129 395/135; and entitled: Integrated Real and Virtual Environment Display System, relates to improvements in so-called "virtual reality" computer systems. The display system described enables the effective integration of computer generated images and real, naturally occurring images in the visual display units which provide the user with his entire visual stimulation. Areas of the user's notional field of view where computer-generated imagery is required (for example the cockpit canopy in an aircraft flight simulator) are colored with a predetermined color or intensity. Two video cameras are provided, each of which is mounted so that its field of view corresponds to a respective one of the notional fields of view of the user's eyes. The signals from the video cameras are analyzed to determine the presence of the predetermined color or intensity, thereby giving an indication that a computer generated image is required for that part of the video camera's field of view. If the predetermined color or intensity is not present, the signal from the video camera is relayed directly to the appropriate one of the visual display units.

U.S. Pat. No. 5,389,865; issued Feb. 14, 1995; assigned to CYBERNET SYSTEMS CORPORATION; classified at USPTO classification 318/568.11 318/568.1 318/590 395/95 901/7 901/9; and entitled: Method and System for Providing a Tactile Virtual Reality and Manipulator Defining an Interface Device Therefor, which provides a tactile virtual reality to a user is present. The position and orientation of the user is utilized to generate a virtual reality force field. Forces are in turn generated on the user as a function of this force field. A six-axis manipulator is presented for providing a user interface to such a system. This manipulator provides a unique kinematic structure with two constant force springs which provide gravity compensation so that the manipulator effectively floats.

U.S. Pat. No. 5,388,990; issued Feb. 14, 1995; assigned to UNITED STATES OF AMERICA, NATIONAL AERONAUTICS AND SPACE ADMINISTRATION; classified at USPTO classification 434/38 345/8 364/578 395/152 434/43 434/307R 434/372; and entitled: Virtual Reality Flight Control Display with Six-Degree-of-Freedom Controller and Spherical Orientation Overlay, teaches a virtual reality flight control system which displays to the pilot the image of a scene surrounding a vehicle or pod having six degrees of freedom of acceleration or velocity control by the pilot and traveling through inertial space. The image itself includes a superimposed figure providing the pilot with an instant reference of orientation consisting of superimposed sets of geometric figures whose relative orientations provide the pilot an instantaneous feel or sense of orientation changes with respect to some fixed coordinate system. They include a first set of geometric figures whose orientations are fixed to the pilot's vehicle and a second set of geometric figures whose orientations are fixed with respect to a fixed or interstellar coordinate system. The first set of figures is a first set of orthogonal great circles about the three orthogonal axes of the flight vehicle or pod and centered at and surrounding the pilot's head, while the second set of figures is a second set of orthogonal great circles about the three orthogonal axes of a fixed or interstellar coordinate system, also centered at and surrounding the pilot's head.

U.S. Pat. No. 5,388,059, issued Feb. 7, 1995; assigned to the UNIVERSITY OF MARYLAND; USPTO classification 364/559 364/516; entitled: Computer Vision System for Accurate Monitoring of Object Pose; teaches a sensing system for accurately monitoring the position and orientation of an object. At least Four (4) point light sources am mounted on the surface of the object. A single electronic camera captures images of the point light sources. Locations of these images am detected in each camera image, and a computer runs an iterative task using these locations to obtain accurate estimates of the pose of the object in a camera coordinate system at video rate. The object is held by an operator for cursor control, for interaction with virtual reality scenes on computer displays, or for remote interactive control of teleoperated mechanisms.

U.S. Pat. No. 5,373,857; issued Dec. 20, 1994; assigned to FORTE TECHNOLOGIES, INC.; USPTO classification 128/782; entitled Head Tracking Apparatus; teaches a low cost head tracker for a virtual reality head set for determining the orientation of the head set relative to the earth's magnetic field includes a magnetic sensor responsive to the earth's magnetic field, and disposed on the head set and arranged with respect to a vertical axis of rotation of the head set to produce a displacement signal relative to the angular displacement of the head set with respect to a calibration orientation relative to the earth's magnetic field, and a signal processor connected to the magnetic sensor, and responsive to the electrical displacement signal for producing an output signal proportional to the orientation of the head set relative to the calibration orientation.

U.S. Pat. No. 5,347,400; issued Sep. 13, 1994; USPTO classification 359/815 345/7 345/8 359/630 359/742 359/813; entitled: Optical System for Virtual Reality Helmet; provides an optical system for a virtual reality head mounted display with improved image quality, enlarged field of view, and enhanced adjustability. In one embodiment, the optical system comprises a housing coupled to the frame of the head mounted display, a pair of displays mounted to the housing each defining a visual plane, and first and second lenses mounted between each of the displays and the user's eyes. The lenses are mounted to the housing such that each lens is disposed at an angle of between One (1) degree, and Fifteen (15) degrees relative to the visual plane. The lenses are also mounted such that the interoptic distance between the lenses may be adjusted. The optical system also has a unique lens construction including a standard Fresnel lens mounted in parallel to a low-diffraction Fresnel lens, resulting in substantially reduced diffractive interference.

U.S. Pat. No. 5,310,349; issued May 10, 1994; assigned to JOSTENS LEARNING CORPORATION; USPTO classification 434/350 345/156 364/419.2 395/152 395/927 434/118 434/307R 434/365; entitled: Instructional Management System; teaches a virtual school user interface running on networked personal computers for providing administrative and instructional functions to users in a scholastic environment. A user selects among grouped system functions by accessing one of a plurality of rooms within a school representation displayed on a video screen, with the networked virtual reality presenting the user as a real-time entity within the virtual school so that the user can interact with other users and system elements. A learning path editor is also provided for allowing users to author student curriculum sequences using graphical icons. A guidance tutor is further provided for coaching a student by displaying a guidance message on the video screen when so indicated by an instructional context. A courseware scheduler is further provided for delivering specific courseware to specific computers during specific time periods. A system monitor is further provided for gathering information in real-time on the state of each computer.

U.S. Pat. No. 5,227,985, issued Jul. 13, 1993; assigned to the UNIVERSITY OF MARYLAND; USPTO classification 364/559 345/158 364/516; entitled: Computer Vision System for Position Monitoring in Three Dimensions Using Non-Coplanar Light Sources attached to a monitored object; teaches a sensing system for monitoring the position and orientation of a rigid object. At least 4 point light sources are mounted on the surface of the object in a noncoplanar arrangement. A single electronic camera captures images of the point light sources. Locations of the images of the light sources are detected in each video image, and a computer runs a task using these locations to obtain close approximations of the rotation matrix and translation vector of the object in a camera coordinate system at video rate. The object is held by an operator for three-dimensional cursor control and interaction with virtual reality scenes on computer displays, and for remote interactive control of teleoperated mechanisms.

U.S. Pat. No. 5,214,615; issued May 25, 1993; USPTO classification 367/128 367/907; entitled: Three-Dimensional Displacement of a Body With Computer Interface; provides a system for tracking the three-dimensional position of an object within a three-dimensional region by triangulation techniques to generate signals corresponding to such three-dimensional positions. The signals may be used to operate a variably operable system to create a virtual reality system. The triangulation means may comprise at least three ultrasound emitters cooperating with ultrasound receivers located on a body moving in the three-dimensional region.

U.S. Pat. No. 5,185,561; issued Feb. 9, 1993; assigned to DIGITAL EQUIPMENT CORPORATION; USPO classification: 318/432 345/156 434/45; entitled: Torque Motor as a Tactile Feedback Device in a Computer System; teaches a hand held, one dimensional, torque feedback device used to feel and manipulate computer generated visual information and associated torque forces. In the preferred embodiment, molecular bond data is manipulated in a virtual reality system. The device can also be used with a workstation generated display on a plurality of problems which generate torque.

U.S. Pat. No. 5,172,313; issued Dec. 15, 1992; USPTO classification 364/401 395/925; Computerized Management System; teaches a computing apparatus for an improved system that manages. The apparatus has computing machinery which includes a computer and an input/output device for two-way communication between the computer and an operator. The computer includes operating instructions for: (a) receiving information from an operator during a management emergence stage necessary for developing a plan in machine readable language including a daily virtual (equivalent) cost for an objective (task/service); (b) processing the plan through a management convergence stage for generating subdivisional plans for output to an operator and receiving performance information as feedback for reducing the objective to a reality; (c) processing the management information and feedback information obtained during the emergence and convergence stages through a proliference stage for generating specifications and quantitative goals for a new version of the objective for processing through the emergence and convergence stages including: (1) analyzing and selectively removing those tasks which have exceeded planned or suspended task time; and (2) performing a system analysis routine for (i) determining the completion of a task required in a most recent series of tasks and directing performance of the next task in the series to avoid duplication; and (ii) calculating the scheduled time for the remaining tasks in the series.

U.S. Pat. No. 5,130,794; issued Jul. 14, 1992; USPTO classification: 348/39 348/383; entitled: Panoramic Display System; teaches a panoramic image based virtual reality display system which includes a panoramic optical assembly, preferably of substantially spherical coverage, feeding composite optical images to a light sensitive surface of a video camera for storage or further processing in image processing circuitry. Such image processing circuitry includes a special effects generator and image segment circuitry to divide a composite image into a plurality of image segments or sub-segments for display on individual displays of multiple video display assemblies. Such a multiple video display assembly preferably includes a closed structure having individual display units mounted in all viewable directions therein, with segments of the composite image displayed on respective display units to recreate the panoramic view gathered by the panoramic optical assembly. The image processing circuitry may also select a portion or portions of the composite image for display on one or two displays of a head mounted display unit.

Various applications of mental visualization are also well known in the prior art, as exemplified by the following references which were found pursuant to a search of the MEDLINE database at the Library of Congress (hereinafter referred to as "LOC"), all of which are incorporated herein by reference in their entireties:

In LOC record number 92196384, dated 1992; entitled: The Use of Hypnosis with Cancer Patients, A. A. Levitan of the University of Minnesota, disclosed that mental visualization through hypnosis has been proven extremely valuable in the treatment of cancer patients. Specific applications include: establishing rapport between the patient and members of the medical health team; control of pain with self-regulation of pain perception through the use of glove anesthesia, time distortion, amnesia, transference of pain to a different body part, or dissociation of the painful part from the rest of the the body; controlling symptoms, such as, nausea, anticipatory emesis, learned food aversions, etc.; psychotherapy for anxiety, depression, guilt, anger, hostility, frustration, isolation, and a diminished sense of self-esteem; visualization for health improvement; and dealing with death anxiety and other related issues. Hypnosis as a means of inducing mental visualization, has unique advantages for patients including improvement of self-esteem, involvement in self-care, return of locus of control, lack of unpleasant side effects, and continued efficacy despite continue use.

In LOC record number 95232172, dated February, 1995; entitled: Effect of Imaging and Actual Tasting a Sour Taste on One Side of the Tongue, P. D. Drummond of the Division of Psychology, Murdoch University, at Perth, Western Australia, disclosed the following experiment: to determine whether mental images can stimulate brainstem reflexes directly, parotid salivation was measured bilaterally in Twenty-Four (24) subjects when they imagined, and actually tasted, a sour taste on one side of the tongue. Salivation increased in both cheeks during unilateral gustatory stimulation; furthermore, the response was greater on the stimulated side than contralaterally, indicating that the gustatory reflex has a unilateral component. Subjects imagined the sour taste more clearly after actually experiencing it. However, salivation did not increase significantly during imagery trials, either before or after exposure to the sour taste. In fact, salivation to imagery decreased below baseline after exposure. These findings suggest that extraneous factors, i.e., the emotional connotation of mental images, anxiety, discomfort, repetitive measurement or fatigue, might sometimes inhibit specific reflex activity induced by metal images.

In LOC record number 95189392; dated October, 1994; entitled Mental Practice of Motor Skills Used in Poststroke Rehabilitation Has Own Effects on Central Nervous System Activation, T. Weiss, et al, of Friedrich Schiller University, Institute of Physiology, Jena, FR Germany, disclosed that in the last few years, it has been shown that the use of EMG triggered electrical myostimulation (ETEM) brings good results in poststroke rehabilitation. It has been hypothesized that the relearning effects obtained by means of ETEM are due to the reinstatement of proprioceptive feedback. However the technique is most powerful if imagination of motor acts, i.e., so-called "mental practice," is used as an initial part of ETEM. Since mental practice in healthy people leads to central nervous activation processes as well as to an improvement of motor skills, the authors investigated the effects of metal practice alone on central nervous activity by means of EEG in stroke patients. Twelve left-sided hemiplegic patients who underwent a specific poststroke rehabilitation treatment were requested to perform a simple arm movement sequence. In the following mental practice period, the patients were requested to imagine the same sequence without any real movement. EEG background activity was recorded during baseline and imagination periods. After the calculation of z-transformed power values within the alpha and beta-1 band, differences between rest and imagination periods were evaluated for significance. Stroke patients demonstrated significant decreases of alpha as well as beta-1 power during metal practice in comparison to the rest period. These changes are similar to those obtained in healthy subjects. Central alpha power diminished only during imagination of the contralateral arm. This phenomenon, as well as the decrease of beta-1 power in central derivation were also obtained during real motor performance and might indicate an activation of the sensorimotor cortex. In accordance with the hypothesis of internal feedback mechanisms, this activation is a necessary prerequisite for motor learning during mental practice. The authors concluded that mental practice of motor skills might have its own effects on poststroke rehabilitation.

In LOC record number 95202933; dated February, 1995; entitled: Neural Adaptation of Imaginary Visual Motion, D. Gilden, et al, of The Department of Psychology, of the University of Texas at Austin, disclosed that observers made time-to-contact judgements about an imagined moving object that passed through an area of the visual field previously adapted to a single direction of real motion. The direction of imagined speed was slowed. When imagined motion was in the same direction as that experienced during adaptation, imagined speed slowed. When imagined speed was in the opposite direction, its speed increased. When adaptation and imagined motions were orthogonal, imagined speed was unaffected. The particular influence that prior adaptation has on imagined speed suggests that motion and real vision may engage common neural mechanisms without being functionally equivalent. Negative aftereffects observed in imagined motion imply that the imagination represents movement as an inference from position changes of static images.

In LOC record number 95049800; dated June, 1994; entitled: Activation Process During Mental Practice in Stroke Patients, T. Weiss, et al, of Friedrich Schiller University, Institute of Physiology, Jena, FR Germany, disclosed that mental practice is known to improve motor performance in health subjects. It is also known to be accompanied by a higher central nervous activity. Since such effects seem to be desirable for rehabilitation, the authors investigated the possibility of detecting changes in central nervous activity by means of EEG in stroke patients, and whether these changes were similar to those observed in healthy subjects. Twelve left-sided hemiplegic patients who underwent a specific post-stroke rehabilitation treatment were requested to perform a simple arm movement sequence. In the following mental practice period, the patients were requested to image the same sequence without any real movement. EEG background activity was recorded during rest and imagination periods. After the calculation of the z-transformed power values within the theta, alpha and beta-1 band, differences between rest and imagination periods were evaluated for their significance. Stroke patients show significant decreases of theta, alpha, as well as beta-1 power during metal practice in comparison to the rest period. These changes are similar to those obtained in healthy patients. Theta power decreases in central and parietal leads. Central alpha power diminishes only during imagination of the contralateral arm this phenomenon, as well as the decrease of beta-1 power in central deviation were also obtained during real motor performance and might indicate an activation of the sensorimotor cortex. In accordance with the hypothesis of internal feedback mechanisms, this activation is a necessary prerequisite for motor learning during mental practice.

In LOC record number 94353191; dated 1994; entitled: Hypnosis and the Allergic Response, J. Wyler-Harper, et al, disclosed that in recent years our knowledge of the immune system and the pathogenesis of immune disorders has increased. There has been much research on the complex connections between the psyche, the central nervous system and the immune system and the effect of mood on disease processes. Their paper reviewed the evidence on the effects of hypnosis on the allergic skin test reaction, on allergies, particularly respiratory allergies and hayfever, and on bronchial hyperactivity and asthma. Hypnosis, which is generally regarded as an altered state of consciousness associated with concentration, relaxation and imagination and amongst other characteristics, an enhanced responsiveness to suggestion, has long been thought to be effective in the amelioration of various bodily disorders. It has seemed that the state of hypnosis is capable of a bridging or mediating function in the supposed dualism between mind and body. There has been great variation in the experimental and clinical procedures such as type of hypnotic intervention employed, the training of subjects and the timing of the intervention. Also, variability in the type of allergen used and its mode of application is evident. But despite these limitations, many of the studies have shown a link between the use of hypnosis and a changed response to an allergic stimulus or to a lessened bronchial hyperactivity. There is yet no clear explanation for the effectiveness of hypnosis, but there is some evidence for an influence on the neurovascular component of the allergic response.

Although virtual reality has been applied to the science of medicine, the literature is sketchy as to the limit and manner of its application, as exemplified by the following references which were found pursuant to a search of the MEDLINE database at the Library of Congress (hereinafter referred to as "LOC"), all of which are incorporated herein by reference in their entireties:

In LOC record number 94171544; dated December, 1993; entitled: Virtual Reality: Applications in Medicine and Psychiatry, E. Camare, of the Department of Psychiatry, John A. Burns School of Medicine, University of Hawaii, disclosed that virtual reality is a coined description of a new computer-based technology that allows the user to enter a 3-D artificial world. Inside this world, the user can look around, move around and interact within computer worlds. The user can fly, visit exotic lands, play with molecules, "enter" cardiac chambers and watch blood swirl or do simulated surgery.

In LOC record number 95208929; dated April 1995; entitled: Effectiveness of Computer-Generated (Virtual Reality) Graded Exposure in the Treatment of Acrophobia, B. O. Rothbaum, et al, disclose a clinical trial, the goal of which was to examine the efficacy of computer-generated (virtual reality) graded exposure in the treatment of acrophobia (fear of heights). The authors concluded that treatment with virtual reality graded exposure was successful in reducing fear of heights.

In LOC record number 95111597; dated August, 1994; entitled: Augmenting Reality in Rehabilitation Medicine, W. J. Greenleaf, of Greenleaf Medical Systems of Palo Alto, Calif., disclosed some potential uses of virtual reality technology to support and augment routine activities for people who have physical disabilities.

In LOC record number 95111600; dated August, 1994; entitled: A Resource Guide to VR in Medicine, T. Emerson, et al, of the Human Interface Technology Laboratory of the University of Washington, Seattle, Wash., provided a bibliography of many of the most noteworthy contributions to the emerging literature about virtual reality in medicine.

In LOC record number 94360023; dated May-June, 1994; entitled: The Technique of Virtual Reality: a New Tool in Research of The Productive Symptoms in Psychiatry, I. Zyss, presented the possibilities of the new computer technique of "virtual reality." It causes a nearly perfect "deception" of the central nervous function of the realizing judgement and can be a tool in research among others into the perception and its disturbances, especially into the productive symptoms in psychiatry.

In LOC record number 94191890; dated April, 1993; entitled: Motor Styill Learning in Cerebral Palsy: Movement, Action and Computer-Enhanced Therapy, J. P. Wann, et al of the Department of Psychology, of the University of Edinburgh, U.K., disclosed the extent to which previous research into movement control can provide key principles on which to model therapy for individuals with severe cerebral palsy. It is suggested that the movement perspective has traditionally stressed the role of implicit knowledge of the dynamic characteristics of the body and that this provides support for the principles of biofeedback training.

The terms "metaphor," and its variants as used herein is best defined by the following references which was found pursuant to a search of the MEDLINE database at the Library of Congress (hereinafter referred to as "LOC"), the entirety of which is incorporated herein by reference:

In LOC record number 94262584; dated April, 1994; entitled: Interacting with Metaphors, S. J. Kingsbury, of the Harvard Medical School, disclosed that creating metaphorical settings in which a patient may therapeutically interact while hypnotized would appear to have many of the advantages of more traditional uses of metaphors and to possess advantages of its own. Although this type of guided imagery may be widely used in practice, it is under-represented in the literature compared to other uses of metaphor. The author describes the use of a castle setting as one example of this type of metaphorical setting that may be useful in working with trauma patients.

In LOC record number 94038054; dated June, 1993; entitled: Healing and the Invention of Metaphor: the Effectiveness of Symbols Revisited, L. J. Kirmayer, of the Division of Social & Transcultural Psychiatry, McGill University, Montreal, Quebec, argued that a theory of meaning adequate to account for the effectiveness of symbolic healing and psychotherapy requires some variant of the three concepts of myth, metaphor and archetype. Myth stands for the overarching narrative structures of the self produced and lent authority by cultural tradition. Archetype stands not for performed ideas or images, but for the bodily-given in meaning. Metaphor occupies an intermediate realm, linking narrative and bodily-given experience through imaginative constructions and enactments that allow movement in sensory-affective quality space. This pluralistic perspective itself constitutes a middle-ground between constructivist and realist approaches to meaning that can integrate causal and interpretive models of symbolic healing.

However, there is no teaching in the prior art of any means and/or method for perfecting the skill of mental visualization in the mind of a subject. Thus there exists a long felt need for such a means and/or method.

It is therefore the primary object of the instant invention to satisfy this long felt need.

SUMMARY OF THE INVENTION

The instant invention provides an article of manufacture comprising a medium with a computer program printed thereon, operable within a virtual reality device which is designed for perfecting mental visualization within the mind of a subject sufficient alone to effect a desired neurological and/or physiological change within the body of said subject, even in the substantial absence of any physical movement by the subject. It also provides the program medium in combination with a virtual reality device and a method of using the same. The steps of the method include: operatively interfacing the program medium with the device and mounting the device on the subject; and, running the program. (Note here that the mounting step may proceed the interfacing step). The program is designed to communicate a dynamic real or metaphoric, or combination of real and metaphoric scenario to the subject which is designed for perfecting mental visualization within the mind of the subject sufficient alone to effect a desired neurological and/or physiological change within the body of the subject, even in the substantial absence of any physical movement by the subject. It can also be further designed to effect preconditioning of the subject's mind, such as inducing a state of meditation or hypnosis, or a combination thereof. The scenario of the program can be designed to exist in real time, real space, compressed time, compressed space, expanded time, expanded space, or any combination thereof. Optionally the program is further designed to enable (motor) interaction between the subject and/or an operator external to the preconditioning and the subject. Although the instant invention primarily contemplates visual stimulation and/or interaction with the subject, is also applicable to visual sense in combination with any one or more of the other senses of the subject.

The term "medium" as used herein is intended to denote any known physical article upon which a computer program may be imprinted, for subsequent transmission to a computer device, including but not limited to a floppy diskette, a tape, a computer hard drive or any other such known computer medium. Here a floppy disk is preferred.

The terms "imprint" and its variants as used herein, is intended to denote any known means by which information is imparted to computer medium, for subsequent transmission to a computer device. Here electronic imprinting of the computer medium is preferred.

The term "interaction" and its variants as used herein, is intended to denote the process by which a subject contributes motor/sensory response to some stimulus provided by the virtual reality program, as well as the response generated through the program in answer to the subject's motor/sensory response.

The term "altered mental state(s)" as used herein, is intended to denote any mental state of a subject other than, his normal waken state.

DETAILED DESCRIPTION OF THE INVENTION

The instant invention can best be described in detail by the following examples:

EXAMPLE 1

A patient has intense pain in his left hand. The pain is treated, by mounting a virtual reality apparatus on the patient. The apparatus is interfaced with a medium having a computer program imprinted thereon. A first optional portion of the program is designed in time and content for perfecting, a state of meditation and/or hypnosis in the mind of the patient by any one of a multitude of well known prior art techniques. The technique is delivered to the patient by plural sensory representation by the program through the apparatus. After the desired altered mental state of the patient is achieved, a second portion of the program is run. This portion of the program provides the patient with a multisensory depiction of a dynamic metaphoric scenario designed to merely augment or completely supplant the patient's ability to control the pain in his hand through mental visualization. The metaphoric scenario depicts, for instance, the inside of a control room, symbolizing the patient's brain. The control room contains a panel having a plurality of conduits leading from it. Each conduit is provided with a label and a switch connected in series with an alarm and/or light, each symbolizing a neural conduit. One of the labels reads: "left hand," symbolizing that this is the nerve leading to the left hand. In order to relieve the pain in his left hand, the patient interacts with the apparatus and program by turning off the switch labeled "left hand." Optionally interaction can be effected by an operator other than the patient. The scenario is designed to play out in real time, real space, compressed time, compressed space, expanded time, expanded space and combinations thereof. The foregoing process is repeated according to a prescribed regimen, until the patient is able to achieve effective unaided mental visualization.

EXAMPLE 2

An athlete desires to improve his technique at the high jump. Mental training is effected, by mounting a virtual reality apparatus on the athlete. The apparatus is interfaced with a medium having a computer program imprinted thereon. A first optional portion of the program is designed in time and content for perfecting, a state of meditation and/or hypnosis in the mind of the athlete by any one of a multitude of well known prior art techniques. The technique is delivered to the athlete by plural sensory representation through the apparatus. After the desired altered mental state of the athlete is achieved, a second portion of the program is run. This portion of the program provides the athlete with a multisensory depiction of a dynamic scenario designed to merely augment or completely supplant the athlete's ability to practice the high jump through mental visualization. The scenario depicts a substantially real particle world depiction of a/the athlete performing a high jump. The athlete interacts with the apparatus and program to perfect his jump. Optionally, interaction can also be effected by a coach. The foregoing process is repeated according to a prescribed regimen, until the athlete is able to achieve mental visualization sufficient for effective mental practice. In this manner the desired neurological and/or physiological changes normally incidental to physical practice can be achieved in the substantial absence of such physical practice.

EXAMPLE 3

A patient suffers from a bloodborne disease such a leukemia. The disease is treated, by mounting a virtual reality apparatus on the patient. The apparatus is interfaced with a medium having a computer program imprinted thereon. A first optional portion of the program is designed in time and content for perfecting, a state of meditation and/or hypnosis in the mind of the patient by any one of a multitude of well known prior art techniques. The technique is delivered to the patient by plural sensory representation through the apparatus. After the desired altered mental state of the patient is achieved, a second portion of the program is run. This portion of the program provides the patient with a multisensory depiction of a dynamic metaphoric scenario designed to merely augment or completely supplant the patient's ability to reduce cancer cells in his blood through his natural physiological mechanisms perfected through mental visualization. The scenario depicts, for instance, a coral reef in a lagoon, symbolizing the interior of the patient's circulatory system. A school of small black fish symbolizing cancer cells, are nibbling away at the coral reef. Another school of large white fish, symbolizing antibodies, enters the scene, and begins to devour the school of black fish. Optionally interaction can be effected by an operator other than the patient. The scenario is designed to play out in real time, real space, compressed time, compressed space, expanded time, expanded space and combinations thereof. The foregoing process is repeated according to a prescribed regimen, until the patient is able to achieve effective mental visualization.

EXAMPLE 4

An professional skater desires to improve his technique at a skating routine. Mental training is effected, by mounting a virtual reality apparatus on the skater. The apparatus is interfaced with a medium having a computer program imprinted thereon. A first optional portion of the program is designed in time and content for perfecting, a state of meditation and/or hypnosis in the mind of the skater by any one of a multitude of well known prior art techniques. The technique is delivered to the skater by plural sensory representation through the apparatus. After the desired altered mental state of the skater is achieved, a second portion of the program is run. This portion of the program provides the skater with a multisensory depiction of dynamic scenario designed to merely augment or completely supplant the skater's ability to practice the skating routine through mental visualization. The scenario depicts a substantially real particle world depiction of a/the skater performing the desired routine. The skater interacts with the apparatus and program to perfect the routine. Optionally, interaction can also be effected by a coach. The foregoing process is repeated according to a prescribed regimen, until the skater is able to achieve mental visualization sufficient for effective mental practice. In this manner the desired neurological and/or physiological changes normally incidental to physical practice can be achieved in the substantial absence of such physical practice.

EXAMPLE 5

A patient suffers from a fractured leg. The condition is treated, by mounting a virtual reality apparatus on the patient. The apparatus is interfaced with a medium with a computer program imprinted thereon. A first optional portion of the program is designed in time and content for perfecting, a state of meditation and/or hypnosis in the mind of the patient by any one of a multitude of well known prior art techniques. The technique is delivered to the patient by plural sensory representation through the apparatus. After the desired altered mental state of the patient is achieved, a second portion of the program is run. This portion of the program provides the patient with a multisensory depiction of a dynamic metaphoric scenario designed to merely augment or completely supplant the patient's ability to promote mending of the fractured bone through physiological mechanisms perfected through mental visualization. The scenario depicts, for instance, a bridge, a span of which has been damaged by an earthquake. A crew of workmen proceeds to reconstruct the span until it is restored, thereby symbolizing the physiological mechanism through which a bone fracture is mended. Optionally interaction can be effected by an operator other than the patient. The scenario is designed to play out in real time, real space, compressed time, compressed space, expanded time, expanded space and combinations thereof. The foregoing process is repeated according to a prescribed regimen, until the patient is able to achieve effective mental visualization.

EXAMPLE 6

A patient suffers from a profound metal depression associated with low self-esteem. The condition is treated, by mounting a virtual reality apparatus on the patient. The apparatus is interfaced with a medium with a computer program imprinted thereon. A first optional portion of the program is designed in time and content for perfecting, a state of meditation, hypnosis and/or altered mental states, in the mind of the patient by any one of a multitude of well known prior art techniques. The technique is delivered to the patient by plural sensory representation through the apparatus. After the desired altered mental state of the patient is achieved, a second portion of the program is run. This portion of the program provides the patient with a multisensory depiction of a dynamic metaphoric scenario designed to merely augment or completely supplant the patient's ability to dispel his profound depression through his own physiological mechanisms perfected through mental visualization. The scenario depicts, for instance, the Nobel prize ceremonies where the patient is about to receive the Nobel humanitarian prize. His acceptance is proceeded by a number of testimonial by others praising his finer qualities. Optionally interaction can be effected by an operator other than the patient. The scenario is designed to play out in real time, real space, compressed time, compressed space, expanded time, expanded space and combinations thereof. The foregoing process is repeated according to a prescribed regimen, until the patient is able to achieve effective mental visualization.

EXAMPLE 7

A stroke patient desires to improve his control and movement over the paralyzed half of his body. Mental training is effected, by mounting a virtual reality apparatus on the patient. The apparatus is interfaced with a medium having a computer program imprinted thereon. A first optional portion of the program is designed in time and content for perfecting, a state of meditation and/or hypnosis in the mind of the patient by any one of a multitude of well known prior art techniques. The technique is delivered to the patient by plural sensory representation through the apparatus. After the desired altered mental state of the patient is achieved, a second portion of the program is run. This portion of the program provides the patient with a multisensory depiction of a dynamic scenario designed to merely augment or completely supplant the patient's ability to practice exercising his effected limbs through mental visualization. The scenario depicts a substantially real particle world depiction of a/the patient performing some physical task otherwise designed to rehabilitate the effected limbs. The patient interacts with the apparatus and program to perfect his rehabilitation. Optionally, interaction can also be effected by a medical care provider. The foregoing process is repeated according to a prescribed regimen, until the patient is able to achieve mental visualization sufficient for effective mental practice. In this manner the desired neurological and/or physiological changes normally incidental to physical practice can be achieved in the substantial absence of such physical practice.

Although the invention has been described with reference to certain preferred examples, it will be appreciated that many variations and modifications may be made within the scope of the broad principles of the invention. Hence, it is intended that the preferred examples and all of such variations and modifications be included within the scope and spirit of the invention, as defined by the following claims.

I claim:

1. A method comprising:
   providing a virtual reality device;
   providing a medium with a program imprinted thereon designed for achieving a goal desired by a subject, operable with the device for presenting to at least the visual senses of the subject; said program including:
   (a) a portion for preconditioning the mind of said subject to a precondition receptive to a dynamic scenario; and,
   (b) said dynamic scenario, that is designed to communicate in chronological order:

(I.) a condition which requires a remedy;
(ii.) a mode for effecting the remedy;
(iii.) the performance of the mode so as to effect the remedy; and,
(iv.) rectification of the condition through the performance of the mode;

for causing mental visualization within the mind of the subject sufficient to enable the subject to achieve the desired goal;

wherein the goal is selected from the group consisting of: physical training, mental training, physical healing, mental healing and combinations thereof;

operatively interfacing the medium with the device and mounting the device on the subject; and, running the program.

2. The method of claim 1, wherein said program is further designed to enable interaction between said subject and/or an external operator, and said device.

3. The method of claim 1, wherein said program is further designed to communicate a metaphoric or real, or combined real and metaphoric scenario to said subject designed for perfecting said mental visualization.

4. The method of claim 3, further comprising: effecting said precondition with the program.

5. The method of claim 4, wherein said precondition is one of the group consisting of meditation, hypnosis, altered mental states, and combinations thereof, and is effected by the program.

6. The method of claim 4, wherein said scenario exists in one of the group consisting of: real time, real space, compressed time, compressed space, expanded time, expanded space and combinations thereof.

7. An article of manufacture for use with a virtual reality device comprising a medium with a program imprinted thereon operable with the device and designed for presenting to at least the visual senses of the subject; said program including:

(a) a portion for preconditioning the mind of said subject to a precondition receptive to a dynamic scenario; and,
(b) said dynamic scenario, that is designed to communicate in chronological order:
 (I.) a condition which requires a remedy;
 (ii.) a mode for effecting the remedy;
 (iii.) the performance of the mode so as to effect the remedy; and,
 (iv.) rectification of the condition through the performance of the mode; for causing mental visualization within the mind of the subject sufficient to enable the subject to achieve the desired goal; wherein the goal is selected from the group consisting of: physical training, mental training, physical healing, mental healing and combinations thereof; when the device is mounted on the subject and the medium is operably interfaced with the device, and the program is caused to run.

8. The article of claim 7, wherein the program is further designed to enable interaction between the subject and/or an external operator, and the device.

9. The article of claim 7, wherein said program is further designed to communicate a metaphoric or real, or combined real and metaphoric, scenario to said subject designed for perfecting said mental visualization.

10. The article of claim 9, wherein said program is further designed to precondition the mind of said subject to a state receptive to said scenario.

11. The article of claim 10, wherein said program is further designed to effect said precondition of said mind by one of the group consisting of meditation, hypnosis, altered mental states or combinations thereof.

12. The article of claim 10, wherein said program is designed to present said scenario in one of the group consisting of: real time, real space, compressed time, compressed space, expanded time, expanded space and combinations thereof.

13. The combination comprising a virtual reality device and a medium with a program imprinted thereon designed for achieving a goal desired by a subject for presenting to at least the visual senses of the subject; said program including:

(a) a portion for preconditioning the mind of said subject to a precondition receptive to a dynamic scenario; and,
(b) said dynamic scenario, that is designed to communicate in chronological order:
 (I.) a condition which requires a remedy;
 (ii.) a mode for effecting the remedy;
 (iii.) the performance of the mode so as to effect the remedy; and,
 (iv.) rectification of the condition through the performance of the mode; for causing mental visualization with the mind of the subject sufficient for enabling the subject to achieve the desired goal wherein; the goal is selected from the group consisting of: physical training, mental training, physical healing, mental healing and combinations thereof; operable within the device when the device is mounted on the subject and the medium is operably interfaced with the device, and the program is caused to run.

14. The combination of claim 13, wherein said program is further designed to enable interaction between said subject and/or an external operator, and said device.

15. The combination of claim 13, wherein said program is further designed to communicate a metaphoric or real, or combined real and metaphoric scenario to said subject designed for perfecting said mental visualization.

16. The combination of claim 15, wherein said program is further designed to effect said precondition of said mind by one of the group consisting of meditation, hypnosis, altered mental states or combinations thereof.

17. The combination of claim 13, wherein said program is designed to present said scenario in one of the group consisting of: real time, real space, compressed time, compressed space, expanded time, expanded space and combinations thereof.

* * * * *

UNITED STATES PATENT AND TRADEMARK OFFICE
CERTIFICATE OF CORRECTION

PATENT NO. : 5,736,986

DATED : April 7, 1998

INVENTOR(S) : Frank Sever, Jr.

It is certified that error appears in the above-identified patent and that said Letters Patent is hereby corrected as shown below:

On the title page, Item[54], the title should read --VIRTUAL REALITY PSYCHOPHYSIOLOGICAL CONDITIONING MEDIUM--.

Signed and Sealed this

Sixteenth Day of May, 2000

Attest:

Q. TODD DICKINSON

*Attesting Officer*  *Director of Patents and Trademarks*